(12) United States Patent
Singh et al.

(10) Patent No.: US 11,136,280 B2
(45) Date of Patent: Oct. 5, 2021

(54) PROCESS AND SYSTEM FOR REMOVAL OF LIGHT ENDS AND NON-CONDENSABLES TO PREVENT BUILDUP IN AN OLEFIN/PARAFFIN MEMBRANE SEPARATION PROCESS

(71) Applicant: UOP LLC, Des Plaines, IL (US)

(72) Inventors: Mander Singh, Barrington, IL (US); Charles P Luebke, Mount Prospect, IL (US); Trung Pham, Mount Prospect, IL (US); Steven Kozup, Chicago, IL (US); Carl Liskey, Chicago, IL (US); Simon E. Albo, Evanston, IL (US); Saadet Ulas Acikgoz, Des Plaines, IL (US); Chunqing Liu, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/425,894

(22) Filed: May 29, 2019

(65) Prior Publication Data

US 2020/0377430 A1    Dec. 3, 2020

(51) Int. Cl.
| | | |
|---|---|---|
| *C07C 7/144* | (2006.01) | |
| *C07C 7/00* | (2006.01) | |
| *C07C 7/10* | (2006.01) | |
| *C07C 11/06* | (2006.01) | |
| *F25J 3/02* | (2006.01) | |

(52) U.S. Cl.
CPC ............... *C07C 7/005* (2013.01); *C07C 7/10* (2013.01); *C07C 7/144* (2013.01); *C07C 11/06* (2013.01); *F25J 3/0219* (2013.01); *F25J 3/0242* (2013.01); *F25J 2205/30* (2013.01); *F25J 2205/80* (2013.01); *F25J 2210/12* (2013.01); *F25J 2215/64* (2013.01)

(58) Field of Classification Search
CPC ........... C07C 7/005; C07C 7/10; C07C 7/144; C07C 11/06; F25J 3/0219; F25J 3/0242; F25J 2205/30; F25J 2205/80; F25J 2210/12; F25J 2215/64
See application file for complete search history.

(56) References Cited

U.S. PATENT DOCUMENTS

| | | | | |
|---|---|---|---|---|
| 3,580,961 | A | * | 5/1971 | Guth et al. ................ C07C 5/46 585/648 |
| 3,586,732 | A | * | 6/1971 | Guth .................... B01J 19/2415 585/656 |

(Continued)

OTHER PUBLICATIONS

Stephan et al. ("Design methodology for a membrane/distillation column hybrid process" Journal of Membrane Science 99 (1995) 259-272) (Year: 1995).*

(Continued)

*Primary Examiner* — Youngsul Jeong
*Assistant Examiner* — Jason Y Chong
(74) *Attorney, Agent, or Firm* — Paschall & Associates, LLC; Mark Goldberg

(57) ABSTRACT

Systems and processes are provided to prevent light ends such as methane, ethylene and ethane from building up in an olefin/paraffin separation system that uses a combination of a membrane and distillation column for this separation. In one embodiment a small stripper column is provided downstream from a selective hydrogenation reactor. In the other embodiment, a surge vessel with a receiver is added to the retentate stream of the membrane unit.

11 Claims, 2 Drawing Sheets

(56) References Cited

U.S. PATENT DOCUMENTS

| | | | | |
|---|---|---|---|---|
| 4,456,779 A | * | 6/1984 | Owen | C10G 29/205 |
| | | | | 585/314 |
| 4,868,342 A | * | 9/1989 | Verson | C07C 9/16 |
| | | | | 568/697 |
| 2004/0182786 A1 | * | 9/2004 | Colling | C07C 7/144 |
| | | | | 210/640 |
| 2008/0209942 A1 | * | 9/2008 | Wang | C07C 7/09 |
| | | | | 62/630 |

OTHER PUBLICATIONS

Corona et al. ("Data-Derived Analysis and Inference for an Industrial Deethanizer" Ind. Eng. Chem. Res. 2012, 51, 13732-13742) (Year: 2012).*

* cited by examiner

PROCESS AND SYSTEM FOR REMOVAL OF LIGHT ENDS AND NON-CONDENSABLES TO PREVENT BUILDUP IN AN OLEFIN/PARAFFIN MEMBRANE SEPARATION PROCESS

TECHNICAL FIELD

This disclosure relates generally to a process and system for separating olefins and paraffins in a membrane system. More specifically, this disclosure relates to methods of preventing the buildup of light ends in propylene stream.

BACKGROUND

Processes incorporating membranes have been developed for purifying streams that comprise a mixture of propane and propylene. It has been found that the gas mixture going to these membranes contains light ends including hydrogen, methane, ethane and ethylene. These light ends become an issue because they can buildup in the system and reduce the performance of either a column overhead compressor or the membrane with product specifications not being met.

Among the processes that produce propylene is fluid catalytic cracking which produces naphtha and crude oil liquid products as well as lighter hydrocarbons and hydrogen. The lighter hydrocarbons may be subjected to a variety of treatments including removal of sulfur compounds through processes such as UOP's Merox process to oxidize mercaptan compounds and being sent through C3/C4 splitters to remove C4 hydrocarbons from a C3/C4 stream and C3 splitters (distillation columns to remove propane). In a prior art process, a deethanizer column is used to remove and recycle C2s.

In a typical prior art FCC process after the products of the process are produced, that include a heavy naphtha product, light cycle oil product and heavy oil product, there are vapor streams that include some lighter hydrocarbons and unstabilized gasoline. The gasoline is removed for treating as is fuel gas. There are C3 and C4 hydrocarbons that are sent for further processing including alkylation or polymerization as well as processes to remove mercaptans such as UOP's Merox process. After removal of the mercaptans, in a typical plant the stream is sent to a C3/C4 splitter to recover the C4 hydrocarbons, followed by the C2 hydrocarbons being removed by a deethanizer as part of an off gas stream and recycled to a gas concentration unit. Then the stream is sent to a C3 splitter to separate propylene and propane.

SUMMARY OF THE INVENTION

In one embodiment, the invention is a process of removing hydrogen and lighter hydrocarbons from a hydrocarbon stream comprising passing a gas stream comprising hydrogen and C1-C3 hydrocarbons to a stripper column to produce a stripper off gas stream from a top section of said stripping column and a bottom stream comprising C3 hydrocarbons, passing said bottom stream through a C3 splitter to produce a second bottom stream comprising propane and a second top stream comprising propylene;
sending said second top stream through a membrane unit to produce a permeate stream comprising a higher concentration of propylene than said second top stream and a retentate stream comprising a higher concentration in propane than said second top stream; and returning said retentate stream to said C3 splitter.

Another embodiment of the invention is a process of removing lighter hydrocarbons from a gas stream comprising sending a gas stream comprising C1 to C3 hydrocarbons to a membrane unit to produce a propylene permeate stream and a retentate stream comprising C1-C3 hydrocarbons; sending said retentate stream to a surge vessel to separate said retentate stream into a propane stream and a surge vessel off gas stream comprising C1 to C2 hydrocarbons; and sending said surge vessel off gas stream to a gas concentration unit.

DETAILED DESCRIPTION OF THE INVENTION

Figure 1:
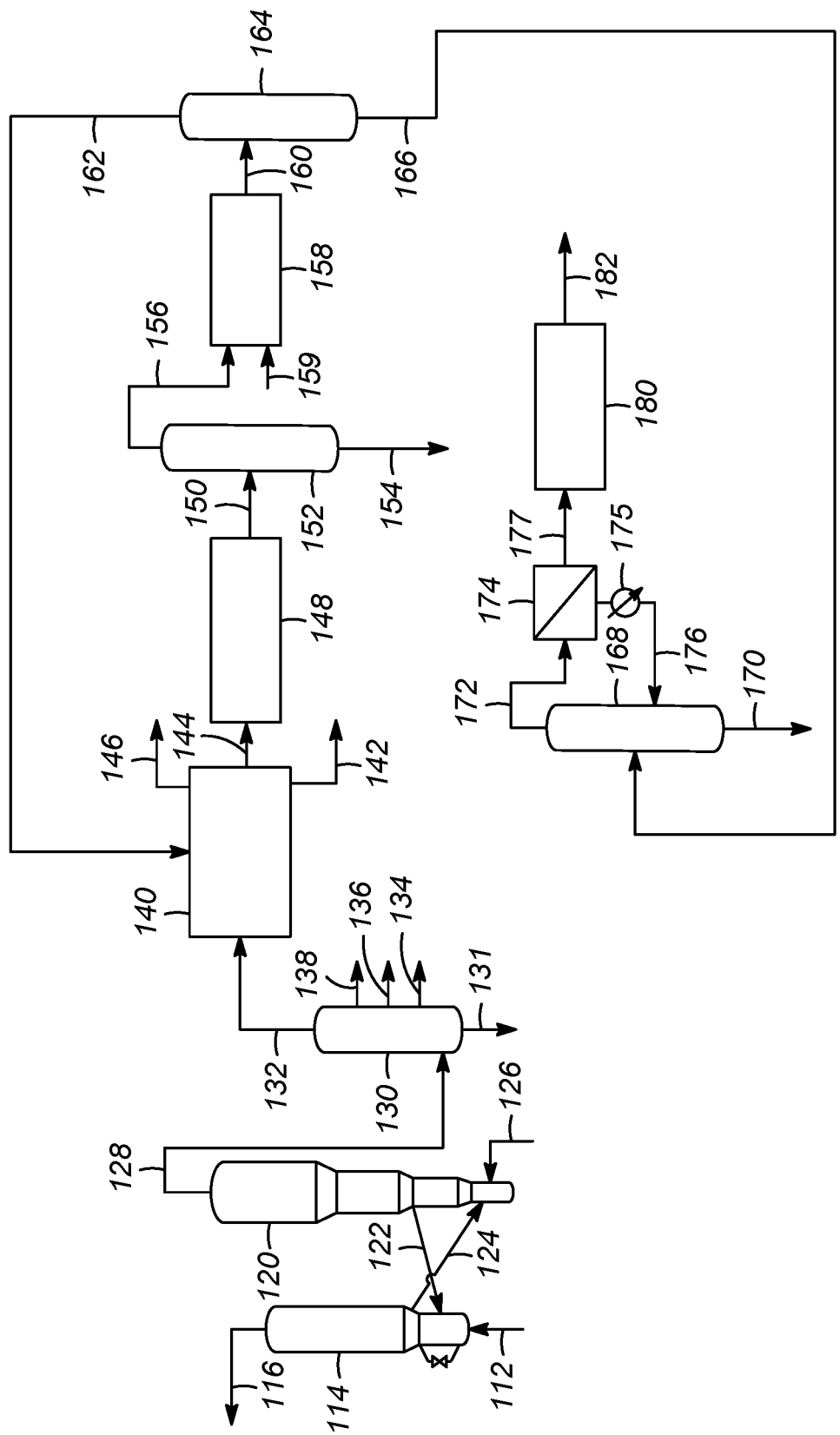
FIG. 1 shows a flow scheme with an added stripper column.

In this invention, there are two alternative methods to remove the light ends from a propylene stream. The first method is to remove them by providing a small stripper column after the selective hydrogenation reactor. The second method is to remove the light ends off the retentate by providing a surge vessel with a packed section for effective separation.

In existing plants, where there is not an existing deethanizer, which removes C2 and lighter components and returning them to the gas concentration unit, it is necessary to include a small stripper column to manage the light ends and non-condensables out of a KLP reactor effluent. The KLP process is a hydrogenation process to convert acetylenic compounds to olefins. The light ends, if not removed, can build up in the C3 splitter overhead and can cause several issues: reduce compressor performance, increase/buildup concentration over time with no outlet (although light olefins, ethylene, can permeate together with C3=), and decrease product purity. The stripper can be operated at 2170-3204 kPa (300-450 psig) pressure, or preferably 2377-2997 kPa (330-420 psig), including 10-30 trays, or preferably 15-25 trays. The stripper can also be a packed (with random/structure packings) column with high efficiency and lower HETP (height equivalent to a theoretical plate) with 5-25 theoretical plates, or preferably 8-22 theoretical plates. With this operating pressure, the overhead condensing temperature is 37.8-65.6° C. (100-150° F.), or preferably 43.3-60° C. (110-140° F.), that can be cooled with supply air or cooling water. Hydrogen and methane can be completely removed in the overhead of the stripper, while C2 hydrocarbons can be removed up to 80-100%, or preferably 90-99%. The C2 concentration in the stripper bottom stream is 0-30 wt ppm, or preferably 2-25 wt ppm.

The second method of removing light ends in the present invention, without using a stripper column, is to install a surge vessel with a receiver on the retentate stream of the membrane. Light end components such as methane and ethane cannot permeate but instead stay with propane. However, if there is no outlet, these components can build up easily in this stream due to a recycle loop going back to the column. Thus, having a surge vessel set a certain temperature provides an outlet for these components and prevents them from building up in the system. Note that any C3 vent together with C1 and C2 in the vent gas stream can be routed back to the Gas Concentration Unit for further C3 recovery (same as deethanizer off gas and stripper off gas treatment). The surge vessel is a receiver with a knock-out water boot and a vertical vent section at the top. The vertical vent section is a packed section/chimney with a height from 0.6-6.1 m (2-20 ft), or preferably 1.2-3.7 m (4-12 ft), diameter of 0.30-1.5 m (1-5 ft), or preferably 0.3-0.9 (1-3 ft). The top of the vertical section, 0.3-3.0 m (1-10 ft), or preferably 0.61-2.4 m (2-8 ft) is chilled with a refrigerant to maintain at 7.2-21.1° C. (45-70° F.), preferably 12.8-18.3° C. (55-65° F.). The refrigerant can be an external refrigerant or an internal process fluid (propylene product) that can be recycled and recompressed and cooled to meet the required chill duty. With the surge vessel, the overall ethane removal is 85-99%, preferably 90-98%. Note that if the acetylene hydrogenation reactor effluent has more than 100 vol ppm ethylene, the first configuration using a stripper is preferable over vent gas stripper due to the fact that ethylene can permeate through the membrane together with C3=. The vent gas stripper can effectively remove ethane even if the acetylene hydrogenation reactor effluent has up to 2800 mol ppm of ethane (or 0.28% mol C2 concentration). The vent gas stripper can also remove any water in the retentate and by accumulating it in the boot section of the equipment. The off gas from the surge vessel has 0.1-20% C2, or preferably 0.5-10% C2 molar concentration and can be routed to the gas concentration unit to recover C3 components. One of skill in the art can vary the order or apply the proposed configurations in various ways. A combination that would be feasible would be combining both configurations having a stripper after the KLP reactor and a vent gas stripper on the retentate stream.

FIG. 1 shows a solution in which a stripper 164 is shown after the selective hydrogenation reactor 158. In FIG. 1, is shown a fluidized catalytic cracking reactor 120 (FCC) into which a fresh hydrocarbon feed 126 is sent to be processed in accordance to a process well known in the art. A regenerator 114 is located next to reactor 120 with air 112 entering together with spent catalyst 122. The catalyst is regenerated and returned through line 124 to reactor 120. A flue gas stream 116 is shown exiting the top of regenerator 114. A stream 128 exits the top of reactor 120 and is sent to a main separation column 130 to be separated into a heavy cycle oil product 134, a light cycle oil product 136 and a heavy naphtha product 138. An overhead stream 132 that contains a mixture of hydrocarbons, hydrogen and unstabilized gasoline exits a top portion of main separation column 130 and is sent to gas concentration unit 140. A fuel gas stream 146, debutanized gasoline stream 142 and a hydrocarbon stream 144 containing C1 to C4 hydrocarbons is sent to a unit 148 to remove mercaptans producing a stream 150 then shown passing to a C3/C4 splitter 152 with a C4 bottoms stream 154 that is sent to storage and a vapor top stream 156 sent for further treatment shown as treaters 158 including a selective hydrogenation reactor in which acetylene is reacted with hydrogen 159. A stream 160 is then sent to a stripper column 164 to produce a lighter off gas stream 162 and a bottoms stream 166 which then is sent to a C3 splitter 168 to produce a propane stream 170 that may be sent to storage (not shown) and a lighter stream 172 that is sent to membrane unit 174. A retentate stream 176 is returned to C3 splitter 168 while a permeate stream 177 is sent to compressor/dryer 180 to produce a propylene stream 182.

Figure 2:
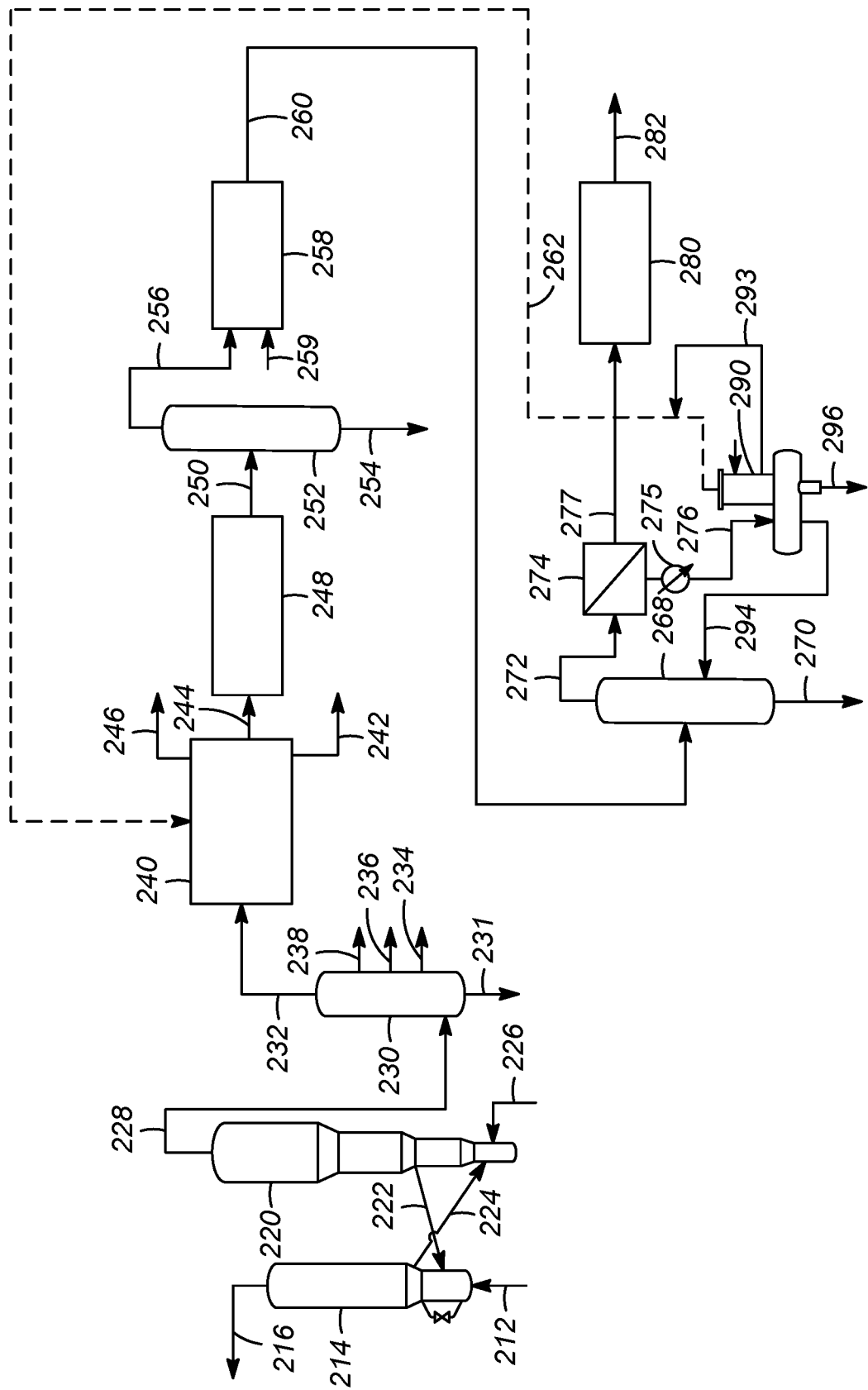
FIG. 2 shows a flow scheme with an added surge vessel.

FIG. 2 shows a solution in which a surge vessel 290 is shown treating the retentate 276 from the membrane unit 274. In FIG. 2, is shown a fluidized catalytic cracking reactor 220 (FCC) into which a fresh hydrocarbon feed 226 is sent to be processed in accordance to a process well known in the art. A regenerator 214 is located next to reactor 220 with air 212 entering together with spent catalyst 222. The catalyst is regenerated and returned through line 224 to reactor 220. A flue gas stream 216 is shown exiting the top of regenerator 214. A stream 228 exits the top of reactor 220 and is sent to a main separation column 230 to be separated into a heavy cycle oil product 234, a light cycle oil product 236 and a heavy naphtha product 238. An overhead stream 232 that contains a mixture of hydrocarbons, hydrogen and unstabilized gasoline exits a top portion of main separation column 230 and is sent to gas concentration unit 240. A fuel gas stream 246, debutanized gasoline stream 242 and a hydrocarbon stream 244 containing C1 to C4 hydrocarbons is sent to a unit 248 to remove mercaptans producing a stream 250 then shown passing to a C3/C4 splitter 252 with a C4 bottoms stream 254 that is sent to storage and a vapor top stream 256 sent for further treatment shown as treaters 258 including a selective hydrogenation reactor in which acetylene is reacted with hydrogen 259. A stream 260 is then sent to a C3 splitter 268 to produce a propane stream 270 that may be sent to storage (not shown) and a lighter stream 272 that is sent to membrane unit 274. A retentate stream 276 is returned to C3 splitter 268 while a permeate stream 277 is sent to compressor/dryer 280 to produce a propylene stream 282. A surge vessel 290 is shown through which passes a retentate gas stream 276 that is first cooled by cooler 275 with most liquids sent through line 294 to C3 splitter 268, water exiting at 296 and optionally being recycled to lighter stream 272 for that stream to have an appropriate humidity level entering membrane unit 274. A vent gas off gas stream 262 returns to gas concentration unit 240. Also shown is inlet 292 for a refrigerant stream, such as propane refrigerant, to enter surge vessel 290 with refrigerant stream 293 exiting surge vessel 290.

Specific Embodiments

While the following is described in conjunction with specific embodiments, it will be understood that this description is intended to illustrate and not limit the scope of the preceding description and the appended claims.

A first embodiment of the invention is a process of removing hydrogen and lighter hydrocarbons from a gas stream comprising passing a gas stream comprising hydrogen and C1-C3 hydrocarbons to a stripper column to produce a stripping off gas stream from a top section of the stripping column and a bottom stream comprising C3 hydrocarbons, passing the bottom stream through a C3 splitter to produce a second bottom stream comprising propane and a second top stream comprising propylene; sending the second top stream through a membrane unit to produce a permeate stream comprising a higher concentration of propylene than the second top stream and a retentate stream comprising a higher concentration in propane than the second top stream; and returning the retentate stream to the C3 splitter. An embodiment of the invention is one, any or all of prior embodiments in this paragraph up through the first embodiment in this paragraph wherein the stripper column is operated at a pressure from about 2170-3204 kPa (300-450) psig pressure and preferably from about 2377-2997 kPa (330-420 psig) pressure. An embodiment of the invention is one, any or all of prior embodiments in this paragraph up through the first embodiment in this paragraph wherein the stripper column includes about 10-30 trays and preferably from about 15-25 trays. An embodiment of the invention is one, any or all of prior embodiments in this paragraph up through the first embodiment in this paragraph wherein the stripper column is packed with packings and contains 5-25 theoretical plates, preferably 8-22 theoretical plates. An embodiment of the invention is one, any or all of prior embodiments in this paragraph up through the first embodiment in this paragraph wherein about 100 wt % of hydrogen and methane and about 80-100 wt % of C2 hydrocarbons are removed in the stripping column and sent in an overhead stream to a gas concentration unit. An embodiment of the invention is one, any or all of prior embodiments in this paragraph up through the first embodiment in this paragraph wherein a stripper bottom stream comprises about 0-30 wt ppm C2 hydrocarbons. An embodiment of the invention is one, any or all of prior embodiments in this paragraph up through the first embodiment in this paragraph wherein the hydrocarbon stream comprising hydrogen and C1-C3 hydrocarbons comprises 0-10 mol % hydrogen and preferably 0-2 mol % hydrogen. An embodiment of the invention is one, any or all of prior embodiments in this paragraph up through the first embodiment in this paragraph wherein the hydrocarbon stream comprising hydrogen and C1-C3 hydrocarbons comprises 0-10 mol % methane, preferably 0-2 mol % methane and 0-10 mol % C2 hydrocarbons, preferably 0-5 mol % C2 hydrocarbons. An embodiment of the invention is one, any or all of prior embodiments in this paragraph up through the first embodiment in this paragraph wherein the hydrocarbon stream comprising hydrogen and C1-C3 hydrocarbons is monitored by analyzers and an online system to monitor and measure $H_2$, $CH_4$, and $C_2$ hydrocarbon concentrations. An embodiment of the invention is one, any or all of prior embodiments in this paragraph up through the first embodiment in this paragraph wherein the stripper off gas stream is in communication with an overhead condenser and a vent condenser. An embodiment of the invention is one, any or all of prior embodiments in this paragraph up through the first embodiment in this paragraph wherein a vent condenser vapor outlet stream comprises 0-10 mol % hydrogen, preferably 0-5 mol % hydrogen and 0-50 mol % C2 hydrocarbons or preferably 0-35 mol % hydrocarbons. An embodiment of the invention is one, any or all of prior embodiments in this paragraph up through the first embodiment in this paragraph wherein the vent condenser vapor is routed to a fuel gas system, vented or routed to the gas concentration unit where ethylene and propylene are recovered. An embodiment of the invention is one, any or all of prior embodiments in this paragraph up through the first embodiment in this paragraph wherein the vent condenser vapor is totally condensed with no detection of condensable gases in the feed stream to the stripper column. An embodiment of the invention is one, any or all of prior embodiments in this paragraph up through the first embodiment in this paragraph wherein the stripper column is operated by bypass of feed stream to the stripper column to direct communication with C3 splitter column.

A second embodiment of the invention is a process of removing hydrogen and lighter hydrocarbons from a gas stream comprising sending a gas stream comprising C1 to C3 hydrocarbons to a membrane unit to produce a propylene permeate stream and a retentate stream comprising C1-C3 hydrocarbons; sending the retentate stream to a surge vessel to separate the retentate stream into a propane stream and a surge vessel off gas stream comprising C1 to C2 hydrocarbons; and sending the surge vessel off gas stream to a gas concentration unit. An embodiment of the invention is one, any or all of prior embodiments in this paragraph up through the second embodiment in this paragraph wherein the surge vessel is a receiver with a knock-out water boot and a vertical vent section at a top section of the surge vessel. An embodiment of the invention is one, any or all of prior embodiments in this paragraph up through the second embodiment in this paragraph wherein the vertical vent section is a packed section having a height from about 0.6 to 6.1 m and preferably from about 0.3 to 0.9 m. An embodiment of the invention is one, any or all of prior embodiments in this paragraph up through the second embodiment in this paragraph wherein a top section of the surge vessel is cooled to about 7.2-21.1° C. An embodiment of the invention is one, any or all of prior embodiments in this paragraph up through the second embodiment in this paragraph wherein the surge vessel off gas stream comprises about 0.5 to 10 mol % C2 hydrocarbons. An embodiment of the invention is one, any or all of prior embodiments in this paragraph up through the second embodiment in this paragraph wherein overall about 85 to 99 wt % of ethane is removed.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process of removing hydrogen and lighter hydrocarbons from a hydrocarbon stream comprising
   a. passing a hydrocarbon stream comprising hydrogen in an amount of more than 0 mol % to about 10 mol % and C1-C3 hydrocarbons to a stripper column to produce a first top stream comprising hydrogen and C1 to C2 hydrocarbons and a first bottom stream comprising C3 hydrocarbons;
   b. passing said first bottom stream through a C3 splitter to produce a second bottom stream comprising propane and a second top stream comprising propylene;
   c. sending said second top stream through a membrane unit to produce a permeate stream comprising a higher concentration of propylene than said second top stream and a retentate stream comprising a higher concentration in propane than said second top stream;
   d. sending said retentate stream to a surge vessel to separate said retentate stream into a propane stream, a water stream, and a surge vessel off gas stream comprising C1 to C2 hydrocarbons; and
   e. returning the propane stream to said C3 splitter.

2. The process of claim 1 wherein said stripper column is operated at a pressure of about 2170-3204 kPa absolute.

3. The process of claim 1 wherein said stripper column includes about 10-30 trays.

4. The process of claim 1 wherein said stripper column is packed with packings and contains 5-25 theoretical plates.

5. The process of claim 1 wherein about 100 wt % of hydrogen and methane and about 80-100 wt % of C2 hydrocarbons in the hydrocarbon stream are removed in said stripper column via the first top stream, and wherein the first top stream is sent to a gas concentration unit.

6. The process of claim 1 wherein the first bottom stream produced from the stripper column comprises about 0-30 wt ppm C2 hydrocarbons.

7. The process of claim 1 wherein the hydrocarbon stream comprising hydrogen and C1-C3 hydrocarbons comprises methane in an amount of more than 0 mol % to about 10 mol % and C2 hydrocarbons in an amount of more than 0 mol % to about 10 mol %.

8. The process of claim 1 wherein the hydrocarbon stream comprising hydrogen and C1-C3 hydrocarbons is monitored by analyzers and an online system to monitor and measure $H_2$, $CH_4$, and $C_2$ hydrocarbon concentrations.

9. The process of claim 1 wherein the first top stream is in communication with an overhead condenser and a vent condenser.

10. The process of claim 9 wherein the vent condenser produces a vent condenser vapor outlet stream comprising hydrogen in an amount of about more than 0 mol % to about 10 mol % and C2 hydrocarbons in an amount of about more than 0 mol % to about 50 mol %.

11. The process of claim 10 wherein the vent condenser vapor outlet stream is routed to a fuel gas system, vented or routed to a gas concentration unit where ethylene and propylene are recovered.

\* \* \* \* \*